United States Patent [19]
Tang et al.

[11] Patent Number: 5,997,529
[45] Date of Patent: Dec. 7, 1999

[54] COMPOUND ASTIGMATIC MYOPIA OR HYPEROPIA CORRECTION BY LASER ABLATION

[75] Inventors: Fuqian Tang; Xiaofeng Han, both of Orlando, Fla.

[73] Assignee: LaserSight Technologies, Inc., Winter Park, Fla.

[21] Appl. No.: 08/957,608

[22] Filed: Oct. 27, 1997

Related U.S. Application Data

[60] Provisional application No. 60/029,790, Oct. 28, 1996.

[51] Int. Cl.$^6$ ................................................. A61B 17/36
[52] U.S. Cl. ....................................................... 606/4; 606/5
[58] Field of Search .............................. 606/4, 5, 13, 10, 606/9; 219/121.6; 600/300, 301, 558

[56] References Cited

U.S. PATENT DOCUMENTS

| | | |
|---|---|---|
| 2,480,737 | 8/1949 | Jayle . |
| 3,074,407 | 1/1963 | Moon . |
| 3,476,112 | 11/1969 | Elstein . |
| 3,697,889 | 10/1972 | Dewey, Jr. . |
| 3,743,965 | 7/1973 | Offner . |
| 3,848,104 | 11/1974 | Locke . |
| 3,938,058 | 2/1976 | Yamamoto . |
| 3,982,541 | 9/1976 | L'Esperance, Jr. . |

(List continued on next page.)

FOREIGN PATENT DOCUMENTS

| | | |
|---|---|---|
| 1243732 | 10/1984 | Canada . |
| 0 151869 A1 | 8/1985 | European Pat. Off. . |
| 0296982A1 | 6/1988 | European Pat. Off. . |
| 0151869B1 | 1/1990 | European Pat. Off. . |
| 0368512A2 | 5/1990 | European Pat. Off. . |
| 0207648B1 | 8/1990 | European Pat. Off. . |
| 0418890A3 | 3/1991 | European Pat. Off. . |
| 0602756A1 | 6/1994 | European Pat. Off. . |

(List continued on next page.)

OTHER PUBLICATIONS

Barraquer, "Lamellar Keratoplasty (special techniques)" Annals of Ophthalmology, Jun. 1972, pp. 437–469.
Burnett, "Company Denies Delay in Approval for Laser", Orlando Sentinel, Feb. 1993, pp. 12–13.
Burnett, "Medical Technology", Orlando Sentinel, Feb. 1993, pp. 1–5.
Gailitis et al., "Solid State Ultraviolet Laser (213 nm) Ablation of the Cornea and Synthetic Collagen Lenticules", Lasers in Surgery and Medicine, Dec. 1991, pp. 556–562.
Gartry et al., "Excimer Laser Photorefractive Keratectomy", Ophthalmology, Aug. 1992, pp. 1210–1219.
Gilbert, "Corneal Topography: In Search of the Excimer Islands", Eye Care Technolgy, Oct. 1993, pp. 23–28.
L'Esperance, "New Laser Systems, Their Potential Clinical Usefulness, and Investigative Laser Procedures", Ophthalmic Lasers, 1989, pp. 995–1045.

(List continued on next page.)

*Primary Examiner*—Linda C. M. Dvorak
*Assistant Examiner*—Roy Gibson
*Attorney, Agent, or Firm*—William H. Bollman; Farkas & Manelli PLLC

[57] ABSTRACT

An apparatus is provided for performing corneal refractive surgery by ablating a portion of a corneal surface of an eye. The apparatus includes a pulsed laser for producing a pulsed output beam of light. A scanning mechanism scans the output beam, and the output beam is operatively associated with the scanning mechanism such that the output beam may be scanned over a predetermined surface defined by a mathematically derived ablation layer boundary curve for each ablation layer. A controller is operatively associated with the scanning mechanism so as to deliver output beams to the predetermined surface such that center points of output beams may be disposed within the ablation layer boundary curve, on the ablation layer boundary curve, and outside but within a predetermined distance from a nearest point on the ablation layer boundary curve so as to integrate the edges of the ablation layer boundary curve to more closely correspond to the desired ablated shape.

52 Claims, 6 Drawing Sheets

U.S. PATENT DOCUMENTS

| | | |
|---|---|---|
| 3,983,507 | 9/1976 | Tang et al. . |
| 4,169,663 | 10/1979 | Murr . |
| 4,180,751 | 12/1979 | Ammann . |
| 4,349,907 | 9/1982 | Campillo et al. . |
| 4,386,428 | 5/1983 | Baer . |
| 4,423,728 | 1/1984 | Lieberman . |
| 4,461,294 | 7/1984 | Baron . |
| 4,477,159 | 10/1984 | Mizuno et al. . |
| 4,520,816 | 6/1985 | Schachar et al. . |
| 4,526,171 | 7/1985 | Schachar . |
| 4,538,608 | 9/1985 | L'Esperance, Jr. . |
| 4,546,773 | 10/1985 | Kremer et al. . |
| 4,573,467 | 3/1986 | Rich et al. . |
| 4,580,559 | 4/1986 | L'Esperance, Jr. . |
| 4,598,714 | 7/1986 | Kremer et al. . |
| 4,619,259 | 10/1986 | Graybill et al. . |
| 4,633,866 | 1/1987 | Peyman et al. . |
| 4,653,495 | 3/1997 | Nanaumi . |
| 4,662,370 | 5/1987 | Hoffman et al. . |
| 4,665,913 | 5/1987 | L'Esperance, Jr. . |
| 4,669,466 | 6/1987 | L'Esperance, Jr. . |
| 4,688,570 | 8/1987 | Kramer et al. . |
| 4,718,418 | 1/1988 | L'Esperance, Jr. . |
| 4,720,189 | 1/1988 | Heyman et al. . |
| 4,721,379 | 1/1988 | L'Esperance, Jr. . |
| 4,729,373 | 3/1988 | Peyman . |
| 4,729,379 | 3/1988 | L'Esperance, Jr. . |
| 4,732,148 | 3/1988 | L'Esperance, Jr. . |
| 4,764,930 | 8/1988 | Bille et al. . |
| 4,770,172 | 9/1988 | L'Esperance . |
| 4,773,414 | 9/1988 | L'Esperance, Jr. . |
| 4,784,135 | 11/1988 | Blum et al. . |
| 4,798,204 | 1/1989 | L'Esperance, Jr. . |
| 4,807,623 | 2/1989 | Lieberman . |
| 4,838,266 | 6/1989 | Koziol et al. . |
| 4,838,679 | 6/1989 | Bille . |
| 4,840,175 | 6/1989 | Peyman . |
| 4,848,340 | 7/1989 | Bille et al. . |
| 4,856,513 | 8/1989 | Muller . |
| 4,862,886 | 9/1989 | Clarke et al. . |
| 4,896,015 | 1/1990 | Taboada et al. . |
| 4,903,695 | 2/1990 | Warner et al. . |
| 4,907,586 | 3/1990 | Bille et al. . |
| 4,911,711 | 3/1990 | Telfair et al. . |
| 4,925,523 | 5/1990 | Braren et al. . |
| 4,941,093 | 7/1990 | Marshall et al. . |
| 4,968,130 | 11/1990 | Hideshima et al. . |
| 4,975,918 | 12/1990 | Morton . |
| 4,993,826 | 2/1991 | Yoder . |
| 4,994,058 | 2/1991 | Raven et al. . |
| 5,019,074 | 5/1991 | Muller . |
| 5,052,004 | 9/1991 | Gratze et al. . |
| 5,063,942 | 11/1991 | Kilmer et al. . |
| 5,065,046 | 11/1991 | Guyer . |
| 5,074,859 | 12/1991 | Koziol . |
| 5,102,409 | 4/1992 | Balgorod . |
| 5,108,388 | 4/1992 | Trokel . |
| 5,108,412 | 4/1992 | Krumeich et al. . |
| 5,133,726 | 7/1992 | Ruiz et al. . |
| 5,144,630 | 9/1992 | Lin . |
| 5,163,934 | 11/1992 | Munnerlyn . |
| 5,163,936 | 11/1992 | Black et al. . |
| 5,182,759 | 1/1993 | Anthon et al. . |
| 5,188,631 | 2/1993 | L'Esperance, Jr. . |
| 5,196,006 | 3/1993 | Klopotek et al. . |
| 5,207,668 | 5/1993 | L'Esperance, Jr. . |
| 5,217,452 | 6/1993 | O'Donnell . |
| 5,219,343 | 6/1993 | L'Esperance, Jr. . |
| 5,219,344 | 6/1993 | Yoder, Jr. . |
| 5,222,960 | 6/1993 | Poley . |
| 5,226,903 | 7/1993 | Mizuno . |
| 5,250,062 | 10/1993 | Hanna . |
| 5,257,988 | 11/1993 | L'Esperance, Jr. . |
| 5,263,950 | 11/1993 | L'Esperance, Jr. . |
| 5,284,477 | 2/1994 | Hanna et al. . |
| 5,288,292 | 2/1994 | Giraud et al. . |
| 5,290,301 | 3/1994 | Lieberman . |
| 5,312,320 | 5/1994 | L'Esperance, Jr. . |
| 5,324,281 | 6/1994 | Muller . |
| 5,334,190 | 8/1994 | Seiler . |
| 5,336,217 | 8/1994 | Buys et al. . |
| 5,345,534 | 9/1994 | Najm et al. . |
| 5,349,590 | 9/1994 | Amirkhanian et al. . |
| 5,350,374 | 9/1994 | Smith . |
| 5,353,262 | 10/1994 | Yakymyshyn et al. . |
| 5,360,424 | 11/1994 | Klopotek . |
| 5,363,388 | 11/1994 | Shi et al. . |
| 5,364,388 | 11/1994 | Koziol . |
| 5,370,641 | 12/1994 | O'Donnell, Jr. . |
| 5,395,356 | 3/1995 | King et al. . |
| 5,395,362 | 3/1995 | Sacharoff et al. . |
| 5,405,355 | 4/1995 | Peyman et al. . |
| 5,411,501 | 5/1995 | Klopotek . |
| 5,423,801 | 6/1995 | Marshall et al. . |
| 5,425,727 | 6/1995 | Koziol . |
| 5,425,729 | 6/1995 | Ishida et al. . |
| 5,437,658 | 8/1995 | Muller et al. . |
| 5,441,511 | 8/1995 | Hanna . |
| 5,442,487 | 8/1995 | Mizuno . |
| 5,445,633 | 8/1995 | Nakamura et al. . |
| 5,461,212 | 10/1995 | Seiler et al. . |
| 5,470,329 | 11/1995 | Sumiya . |
| 5,474,548 | 12/1995 | Knopp et al. . |
| 5,480,396 | 1/1996 | Simon et al. . |
| 5,505,723 | 4/1996 | Muller . |
| 5,507,741 | 4/1996 | L'Esperance, Jr. . |
| 5,507,799 | 4/1996 | Sumiya . |
| 5,520,679 | 5/1996 | Lin ................................ 606/5 |
| 5,549,597 | 8/1996 | Shimmick et al. . |
| 5,556,395 | 9/1996 | Shimmick et al. . |
| 5,582,752 | 12/1996 | Zair . |
| 5,599,340 | 2/1997 | Simon et al. . |
| 5,613,965 | 3/1997 | Muller . |
| 5,624,436 | 4/1997 | Nakamura et al. . |
| 5,634,920 | 6/1997 | Hohla . |
| 5,637,109 | 6/1997 | Sumiya . |
| 5,646,791 | 7/1997 | Glockler . |
| 5,651,784 | 7/1997 | Klopotek . |
| 5,683,379 | 11/1997 | Hohla . |
| 5,684,562 | 11/1997 | Fujieda . |
| 5,711,762 | 1/1998 | Trokel . |
| 5,713,892 | 2/1998 | Shimmick . |
| 5,735,843 | 4/1998 | Trokel . |
| 5,779,696 | 7/1998 | Berry et al. ............................... 606/16 |
| 5,782,822 | 7/1998 | Telfair et al. ............................. 606/5 |
| 5,849,006 | 12/1998 | Frey et al. ................................ 606/5 |
| 5,865,830 | 2/1999 | Parel et al. . |

FOREIGN PATENT DOCUMENTS

| | | |
|---|---|---|
| PCT/FR8700139 | 11/1987 | WIPO . |
| PCT/US9209625 | 5/1993 | WIPO . |
| PCT/US9300327 | 8/1993 | WIPO . |
| PCT/US94/02007 | 9/1994 | WIPO . |
| PCT/EP95/01287 | 10/1995 | WIPO . |

OTHER PUBLICATIONS

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technolgies, Jun. 1992, pp. 266–275.

Marguerite B. McDonald et al, "Central Photorefractive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofiling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser in Situ Keratomileusis and Photorefractive Keratectomy for Correction of High Myopia", Journal of Refractive and Corneal Surgery, Sep. 1994, pp. 498–510.

Ren et al, "Corneal Refractive Surgery Using an Ultra–Violet (213nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blind Human Eyes" Refractive and Corneal Laser Surgery, Jun. 1990, pp. 165–173.

Serdarevic, "Corneal Laser Surgery", Ophthalmic Lasers, 1989, pp. 919–970.

Steinert et al, "Laser Corneal Surgery", Laser Research Laboratory, 1998, pp. 151–154.

Thompson et al, "Philosophy and Technique for Excimer Laser Phototheraputic Keratectomy", Refractive and Corneal Surgery, Apr. 1993, pp. 81–85.

Trokel et al Excimer Laser Surgery of the Cornea, American Journal of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Sep. 1991, pp. 1338–1347.

Qiushi Ren, Raymond P. Galitis, Keith P. Thompson, & J.T. Lin, "Ablation of the Cornea and Synthetic Polymers Using a UV (213 nm) Solid State Laser", IEEE Journal of Quatum Electronics, Dec. 1990, pp.2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communicaitons, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta-BaB_2O_4$, Applied Physics Letters, May 1989, pp. 1206–1208.

Conference on Lasers and Electro–Optics, Optical Society of America, Apr. 1989, p. 390.

FIG. 8A (1) PRIOR ART

COMPOUND ASTIGMATIC MYOPIA OR HYPEROPIA CORRECTION BY LASER ABLATION

This application claims priority from U.S. Provisional application No. 60/029,790, filed on Oct. 28, 1996, the specification of which is incorporated in its entirety herein.

BACKGROUND OF THE INVENTION

1. Field of the Invention

This invention relates to an apparatus for refractive correction utilized to ablate corneal tissue to reshape the corneal surface, and more particularly, to apparatus for corneal re-profiling by laser ablation for correction of myopia, hyperopia, astigmatic myopia and astigmatic hyperopia conditions.

2. Description of Related Art

With reference to FIG. 1, a schematic illustration of a normal eye is shown, wherein light rays 10 pass through the cornea 12 of eye 14 through lens 16 to the retina 18. In a normal eye, the focal point 20 of the light rays occurs on the retina 18 for normal vision.

Common vision defects occur when the focal point 20 is not disposed on the retina 18. For example, as shown in FIG. 2, myopia occurs when the focal point 20 is disposed in front of the retina 18. Myopia may be corrected as shown in FIG. 3 by using conventional methods by ablating tissue 24 of the cornea 12 so as to increase the radius of curvature of cornea 12 to shift the focal point 20 to be on the retina 18.

With reference to FIG. 4, hyperopia occurs when the shape of the cornea does not permit the light rays 10 to focus on the retina 18. Instead, the focal point 20 of the light rays 10 in an eye suffering from hyperopia is disposed behind the retina 18. As shown in FIG. 5, hyperopia can be corrected by ablating tissue 24 of the cornea 12 so as to decrease the radius of curvature of the center of the cornea 12, shifting the focal point 20 to be on the retina 18.

FIGS. 6 and 6A illustrate myopic astigmatism. As shown in FIG. 6, x-direction light rays 10' and y-direction light rays 10" pass through the cornea 12 and lens 16 to the retina 18. However, due to the shape of the cornea 12, the x-direction light rays 10' focus at focal point 20', while the y-direction light rays 10" focus at focal point 20" in front of the retina 18, causing vision to be blurred. FIG. 6A is a three-dimensional illustration of the light rays 10' and 10" passing through the cornea 12 and showing the location of the focal points 20' and 20". Myopic astigmatism can be corrected by re-profiling the surface of the cornea 12 to obtain a single focal point on the retina 18. It can be appreciated that in hyperopic astigmatism, the focal points 20' and 20" of the x-direction and y-direction light rays, respectively, are behind the retina. Hyperopic astigmatism may also be corrected by corneal re-profiling.

When correcting conditions such as, for example, myopia, hyperopia and/or astigmatism, the eye may be ablated in thin layers by an excimer laser or the like to achieve the desired correction. For simple myopic correction, the shape of each layer of the ablation is represented by the equation for a circle. Parabolic, spherical or other mathematical models could be used. For a small laser beam to ablate each layer of the corneal tissue, the laser beam must be scanned across the surface of the eye, inside of and on the curve defining the zone of ablation. Many approaches can be used to scan each layer. The scanning process may be defined as linear, circular, random multi-beam, or other useable method.

However, when employing a mathematically modeled curve to define each layer of ablation in performing laser vision corrections, and when the center of each laser pulse is positioned inside of or at the boundary of the curve, the effective ablation area for each layer may be smaller than that defined by the actual curve modeled because of the incremental movement of the laser. Thus, the correction may not be as effective as theorized.

Accordingly, there is a need to provide an apparatus that controls laser pulse center point positions effectively throughout a layer of ablation.

SUMMARY OF THE INVENTION

It is an object of the invention to fulfill the need referred to above. In accordance with the principles of the present invention, this object is obtained by providing an apparatus and method for performing corneal refractive surgery by ablating a portion of a corneal surface of an eye. The apparatus includes a pulsed laser for producing a pulsed output beam of light. A scanning mechanism scans the output beam, and the output beam is operatively associated with the scanning mechanism such that the output beam may be scanned over a predetermined surface defined by a mathematically derived curve. Focusing structure focuses the output beam onto the predetermined surface to a predetermined, generally fixed spot size. A controller is operatively associated with the scanning mechanism so as to deliver output beams to the predetermined surface such that center points of output beams may be disposed within an ablation layer defined by the curve, on the boundary of the ablation layer, and at certain locations outside of the ablation layer so as to ablate the predetermined surface substantially corresponding to an area enclosed by the curve. A method of controlling the above described apparatus is also disclosed.

BRIEF DESCRIPTION OF THE DRAWINGS

Features and advantages of the present invention will become apparent to those skilled in the art from the following description with reference to the drawings, in which:

FIG. 8A(1) is an enlarged view of the encircled portion A of FIG. 8A;

DETAILED DESCRIPTION OF THE PRESENTLY PREFERRED EXEMPLARY EMBODIMENTS

Figure 1:
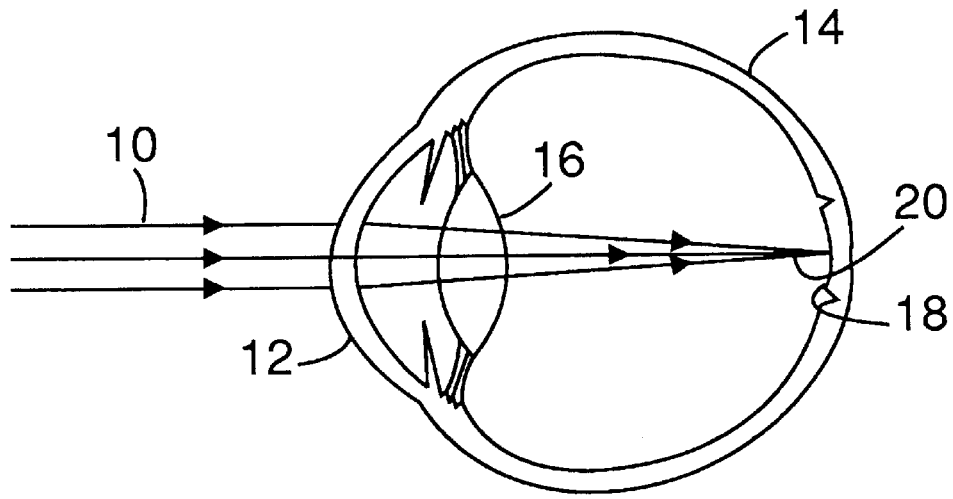
FIG. 1 is a schematic illustration of a normal eye showing light passing through the cornea and lens and focusing at the retina.
Figure 2:
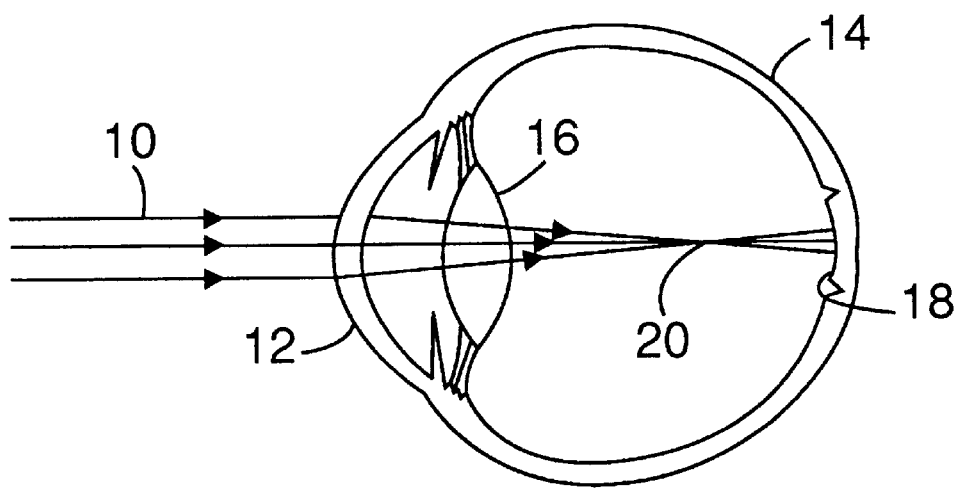
FIG. 2 is a schematic illustration of an eye having a myopia condition wherein the focal point is disposed internally within the eye and not at the retina.
Figure 3:
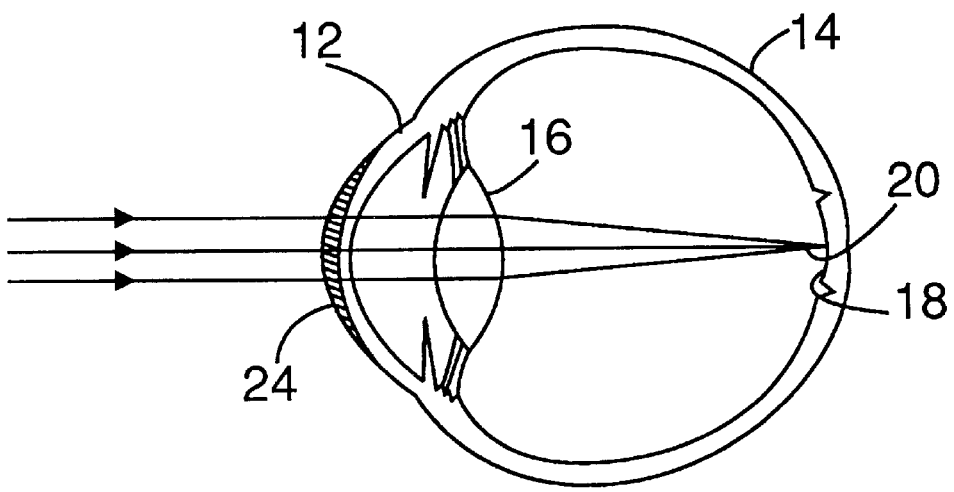
FIG. 3 is a schematic illustration of the eye of FIG. 2 after ablation of the cornea thereby correcting the myopia condition.
Figure 4:
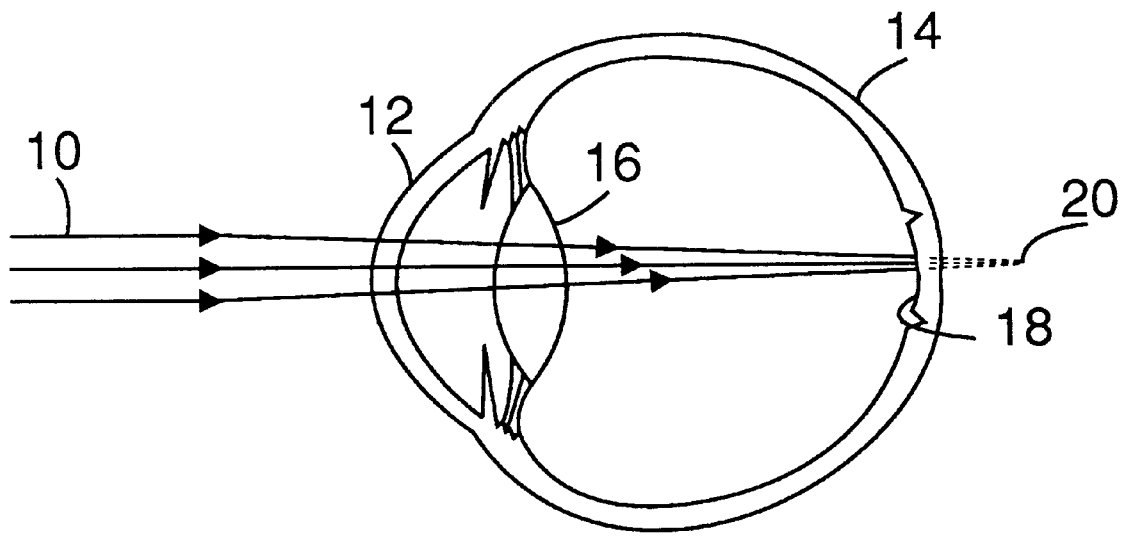
FIG. 4 is a schematic illustration of an eye having a hyperopia condition wherein the focal point occurs outside of the eye.
Figure 5:
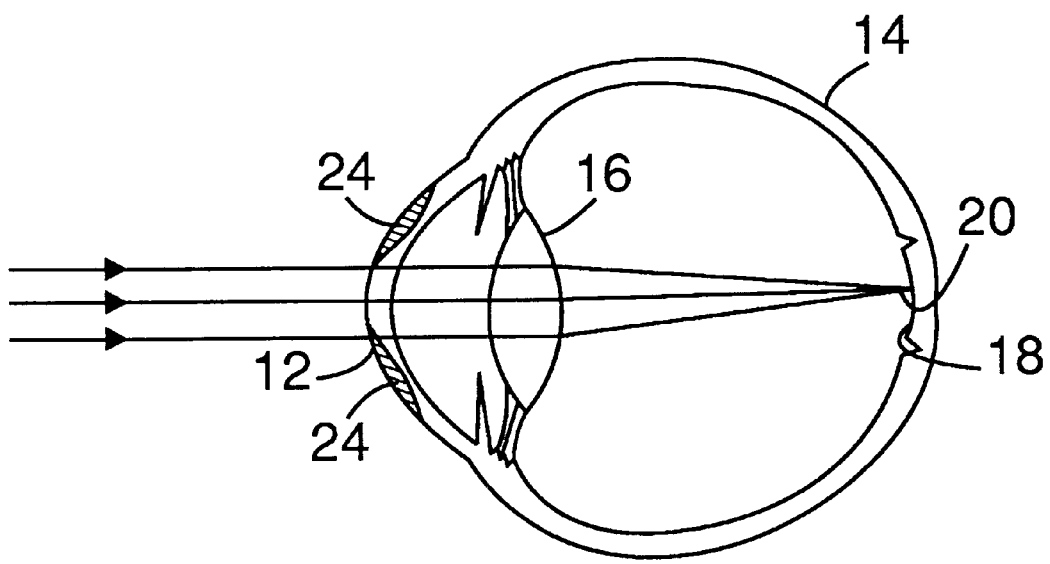
FIG. 5 is a schematic illustration of the eye of FIG. 4 after ablation of the cornea thereby correcting the hyperopia condition.
Figure 6A:
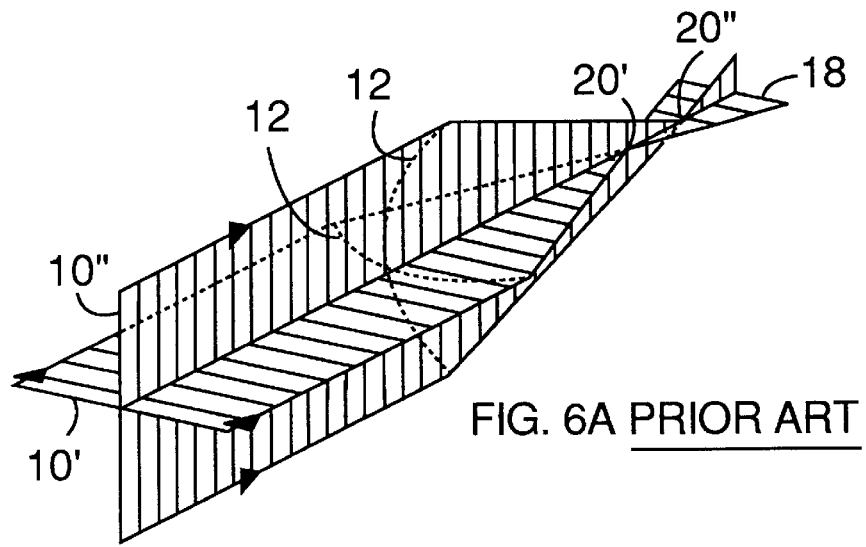
FIG. 6A is a three dimensional schematic illustration of the x and y direction light rays entering the eye of FIG. 6.
Figure 6:
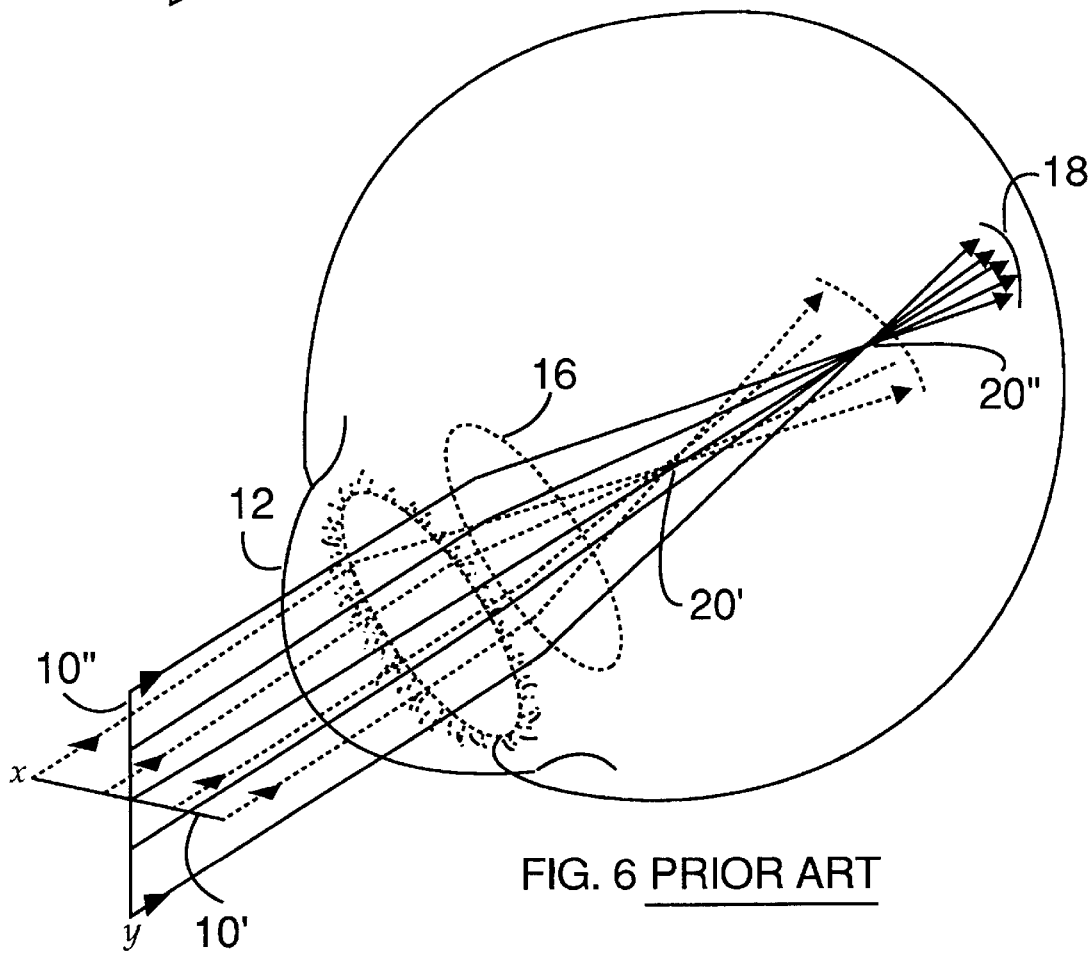
FIG. 6 is an illustration of an eye having myopic astigmatism wherein x-direction light rays and y-direction light rays focus at separate points within the eye and not at the retina.

To understand correction of a corneal defect, theoretical background is as follows.

If $Z_1(x,y)+c_1$ describes the initial corneal surface of an eye, and $Z_2(x,y)+c_2$ describes the corneal surface after ablation, then the ablation depth $D(x,y)$ is defined by:

$$D(x,y) = Z_1(x,y) - Z_2(x,y) + c. \quad \text{(Equation 1)}$$

In Equation 1, the xy-plane is parallel to the tangential plane at the apex of the eye, and the origin of the xy-plane is the center point of the ablation. Constants $c_1$ and $c_2$ are related to the origin of the coordinate system. The constant c in Equation 1 is dependent on the zone size (or depth) of ablation. Constant c may be computed from a set of default conditions.

If it is assumed that the eye is ablated by thin layers by an excimer laser or the like to achieve the desired correction, and the thickness of each thin layer is $\Delta$, the ablation for the nth layer is, following Equation 1:

$$n\Delta = Z_1(x,y) - Z_2(x,y) + c. \quad \text{(Equation 2)}$$

No matter how the eye surface is modeled for simple myopic correction the shape of each layer of ablation is represented by the equation for a circle. Simple myopic correction requires a symmetric model of the eye surface and each cross-section, or layer, is a circle as represented by Equation 2. Also, the equations for $Z_1(x,y)$ and $Z_2(x,y)$ depend on how the surface of the eye is modeled. Parabolic, spherical, or other models could be used. For example, if the eye surface is considered to be a symmetric paraboloid before and after the corrective surgery, $Z_1(xy)$ and $Z_2(x,y)$ may be represented by the following equations:

$$Z_1(x,y) = -\frac{1}{2R_1}(x^2+y^2) + c_1. \quad \text{(Equation 3)}$$

$$Z_2(x,y) = -\frac{1}{2R_2}(x^2+y^2) + c_2.$$

The new equation for the depth of ablation can now be redefined as $$D(x,y) = -\frac{1}{2}\left(\frac{1}{R_1} - \frac{1}{R_2}\right)(x^2+y^2) + \frac{Z_0^2}{8}\left(\frac{1}{R_1} - \frac{1}{R_2}\right) \quad \text{(Equation 4)}$$

where $R_1$ is the initial radius of curvature of the eye at the apex, $R_2$ is the radius of curvature after the surgery, and $Z_0$ is the ablation zone diameter. The constant c from Equation 2, which is also the total depth of ablation at the center (0,0), is represented as the second term on the right hand side of Equation 4.

Another example for the model of the eye surface is a spherical model both before and after ablation. In this case, the following equations are developed:

$$Z_1(x,y) = \sqrt{R_1^2 - x^2 - y^2} + c_1, \quad \text{(Equation 3')}$$

$$Z_2(x,y) = \sqrt{R_2^2 - x^2 - y^2} + c_2,$$

$$D(x,y) = \sqrt{R_1^2 - x^2 - y^2} - \sqrt{R_2^2 - x^2 - y^2} + \sqrt{R_2^2 - \frac{Z_0^2}{4}} - \sqrt{R_1^2 - \frac{Z_0^2}{4}}. \quad \text{(Equation 4')}$$

However, no matter how the eye surface is modeled, Equation 1 can be simplified with a parabolic equation with a certain amount of error. Equation 4 is already a parabolic equation for the parabolic model. For a spherical model, Equation 1 can be simplified by approximating Equation 4' with the following:

$$D(x,y) \approx D_0 - \frac{1}{2}\left(\frac{1}{R_1} - \frac{1}{R_2}\right)(x^2+y^2) \quad \text{(Equation 5)}$$

where $D_0$ is the total depth of ablation, given by $$D_0 = \sqrt{R_2^2 - \frac{Z_0^2}{4}} - \sqrt{R_1^2 - \frac{Z_0^2}{4}} - (R_2 + R_1)$$

Since Equation 2 defines the equation for a circle, the layered ablation process is very easy to control. Since the model used for simple myopia must be radially symmetrical, it can be simplified from three dimensional to two dimensional, as shown by Equations 3', 4' and 5. Astigmatic myopia is a different case because the ablation zone is not circular.

For a small laser beam to ablate each layer of the corneal tissue, the laser beam must be scanned across the surface of the ablation layer of the eye. The scanning process may be linear, circular, multibeam, or any other usable method. The point-by-point computation of the ablation points within the ablation layer is relatively straight forward because the ablation zones for each ablation layer for the correction of simple myopia are defined by circles. A simple ablation method can be designed following the symmetry of each layer. The laser is focused at points following parallel lines (linear scan) across the layer, or can follow concentric circle patterns (circular scan), spiral patterns (spiral scan), or other approaches.

Figure 7A:
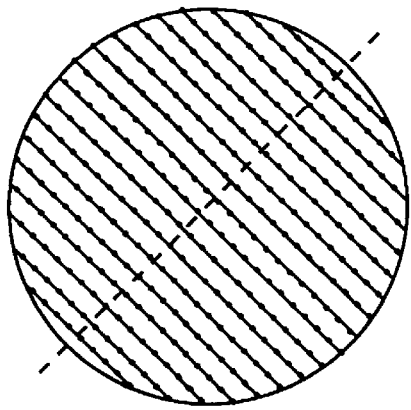
FIGS. 7A and 7B are illustrations of conventional scanning patterns for a linear scan and a circular scan approach, respectively, for the treatment of myopia.
Figure 7B:
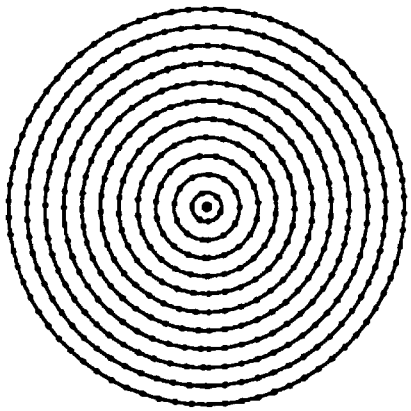

FIG. 7A illustrates an example of a conventional linear scan approach and FIG. 7B illustrates an example of a conventional circular scan approach. Each point only indicates the center of a laser beam, not the size of the laser beam. It can be appreciated from FIGS. 7A that the conventional linear scan pattern is roughly symmetric about a line which is positioned perpendicular to and disposed through the center of the circular layer. The conventional circular scan, on the other hand, is symmetric about the center of the ablation layer.

The most general case is when the initial and final corneal surfaces are modeled asymmetrically (such as an ellipsoid) about the center of treatment. In such general cases, both $Z_{g1}(x,y)$ and $Z_{g2}(x,y)$ which define the initial and final surfaces, respectively, are complicated expressions for complicated surface shapes. The new ablation depth equation is represented as:

$$D_g(x,y) = Z_{g1}(x,y) - Z_{g2}(x,y) + c \qquad \text{(Equation 6)}$$

Similar to Equation 2 each layer of ablation is defined as:

$$n\Delta = Z_{g1}(x,y) - Z_{g2}(x,y) + c. \qquad \text{(Equation 7)}$$

Figure 8A:
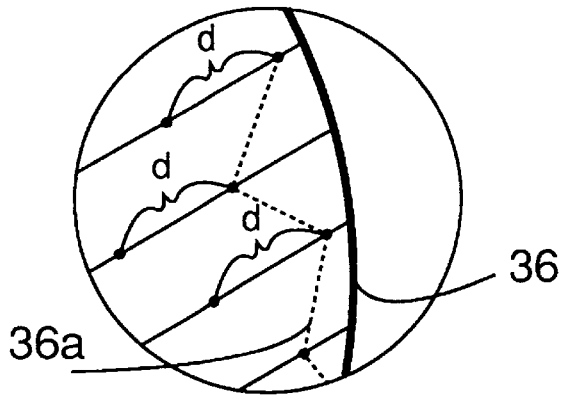
FIGS. 8A and 8B are illustrations of conventional scanning patterns for a linear scan and a circular scan approach, respectively, for the treatment of astigmatic myopia.
Figure 8A:
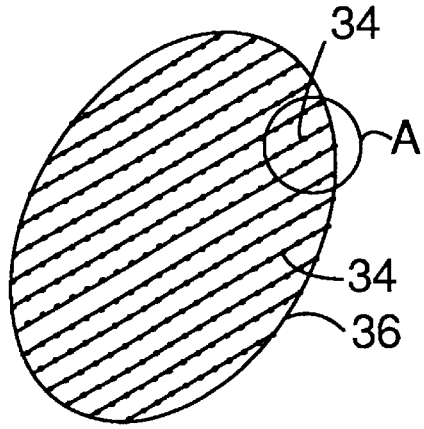
Figure 8B:
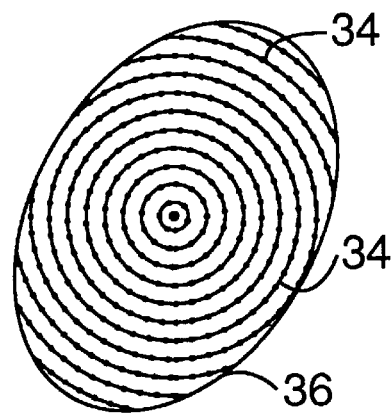

Unlike Equation 2, however, Equation 7 is not an equation for a circle. It is an enclosing curve which more closely resembles an ellipse. Equation 7 defines the ablation layer as an oval layer for the more general case. It can become considerably more complex in the case where x and y are substituted by expressions in terms of other variables. This occurs, for example, when the linear scan is rotated for each layer so that x and y are expressed by two other variables of another orthogonal basis coordinate system. It is difficult to plot the shape of each layer to be ablated without significant computation and time. Even if the shape is determined by computation, it is still difficult to control the ablation because of the time required for the computations, and because the process is not symmetric for either the linear or circular scan, as shown in FIGS. 8A and 8B. It is therefore difficult to devise a method to control the ablation.

If the eye surface is modeled for astigmatic myopia before and after surgery as asymmetric parabolic surfaces, the following equations are developed:

$$Z_{g1}(x, y) = -\frac{1}{2}\left(\frac{x^2}{R_{1x}} + \frac{y^2}{R_{1y}}\right) + c_1. \qquad \text{(Equation 8)}$$

$$Z_{g2}(x, y) = -\frac{1}{2}\left(\frac{x^2}{R_{2x}} + \frac{y^2}{R_{2y}}\right) + c_2.$$

Therefore, Equations 6 and 7 become:

$$D(x, y) = -\frac{1}{2}\left(\frac{x^2}{R_{1x}} + \frac{y^2}{R_{1y}}\right) + \frac{1}{2}\left(\frac{x^2}{R_{2x}} + \frac{y^2}{R_{2y}}\right) + c \qquad \text{(Equation 9)}$$

and $$n\Delta = -\frac{1}{2}\left(\frac{x^2}{R_{1x}} + \frac{y^2}{R_{1y}}\right) + \frac{1}{2}\left(\frac{x^2}{R_{2x}} + \frac{y^2}{R_{2y}}\right) + \frac{Z_y^2}{8}\left(\frac{1}{R_{1y}} - \frac{1}{R_{2y}}\right) \qquad \text{(Equation 10)}$$

where the R's represent the radii of curvature of the eye, the subscripts 1 and 2 specify before and after the ablation, respectively, and x, y, and z specify the coordinates along the x-axis, y-axis, and z-axis, respectively. It is assumed that the radius of curvature before the ablation is smallest along the x-axis, and largest along the y-axis. $Z_y$ is the ablation zone size in the y direction. The model is not radially symmetric, but it is symmetric across the axes.

The preferred model used in the exemplary embodiment of the present invention models the eye surfaces before and after surgery as toruses, and are represented by the following equations:

$$Z_{g1}(x, y) = \sqrt{\left(\sqrt{R_{1x}^2 - x^2} + R_{1y} - R_{1x}\right)^2 - y^2} + c_1, \qquad \text{(Equation 8')}$$

and $$Z_{g2}(x, y) = \sqrt{\left(\sqrt{R_{2x}^2 - x^2} + R_{2y} - R_{2x}\right)^2 - y^2} + c_2.$$

Equations 6 and 7 now become:

$$D(x, y) = \sqrt{\left(\sqrt{R_{1x}^2 - x^2} + R_{1y} - R_{1x}\right)^2 - y^2} - \sqrt{\left(\sqrt{R_{2x}^2 - x^2} + R_{2y} - R_{2x}\right)^2 - y^2} + c \qquad \text{(Equation 9')}$$

and $$n\Delta = \sqrt{\left(\sqrt{R_{1x}^2 - x^2} + R_{1y} - R_{1x}\right)^2 - y^2} - \sqrt{\left(\sqrt{R_{2x}^2 - x^2} + R_{2y} - R_{2x}\right)^2 - y^2} + \sqrt{R_{2y}^2 - \frac{Z_y^2}{4}} - \sqrt{R_{1y}^2 - \frac{Z_y^2}{4}} \qquad \text{(Equation 10')}$$

The model used for astigmatic myopia can be readily applied to simple myopia. In other words, simple myopia is merely a special case of astigmatic myopia, wherein $R_x = R_y$, reducing Equations 10 and 10' to the equations of circles. Other models such as ellipsoid eye surfaces may be used to model the surface of the eye requiring treatment for astigmatic myopia, and the mathematical treatment is similar.

To correct astigmatic myopia or astigmatic hyperopia, the laser ablation of the cornea must make different diopter changes in different directions. This way, the patient becomes non-astigmatic, without myopia or hyperopia.

Figure 9:
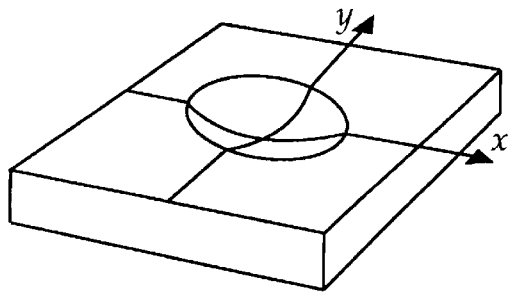
FIG. 9 is an illustration of an ablation if it were a flat surface for an eye having a conventional circular ablation layer to correct for simple myopia.
Figure 10:
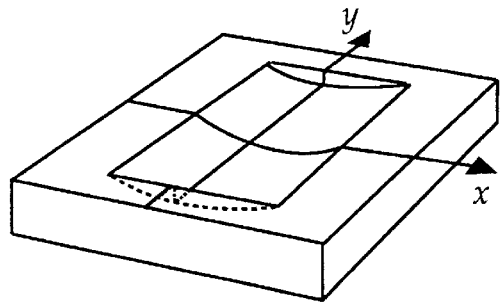
FIG. 10 is an illustration of an ablation if it were a flat surface of an eye having a conventional cylindrical-like ablation layer to correct for astigmatism.

In the case of astigmatic myopia with the x-axis as the steeper axis, the ablations, when illustrated on a flat surface, are shown in two steps in FIGS. 9 and 10. A first series of circular ablation layers correct for the myopia (FIG. 9) or hyperopia and an additional series of cylindrical-shape or other ablation layers (FIG. 10) correct the astigmatism. In this approach, the total depth of the ablation in the center is the sum of the two corrections, and the tissue removed is also the sum of the two corrections. Unfortunately, the amount of tissue removed and the amount of time of the ablation are large. Clearly, this two step approach for correcting astigmatic myopia is not desirable, but until now was a practical answer to the problem solved by the present invention. For example, high diopter patients require deep ablation. In this instance, this two step approach can be severely limited due to the total ablation depth required. As a result, the patient may not be treated fully for both the astigmatism and the myopia or hyperopia.

A new mathematical approach to control the ablation of corneal tissue for the correction of both the astigmatism and the myopia and hyperopia condition has been known to exist. However, as will be shown, this approach continues to require the solving of complicated equations, requiring too much time and computational power.

To illustrate this mathematical approach, the simple myopia case is considered once again. As discussed previously, Equation 2, describes a single nth layer ablation which can be reduced to a circle equation of the form:

$$R^2 - (x^2 + y^2) = 0 \quad \text{(Equation 11)}$$

where R is the radius. By slightly modifying Equation 11, the following relationship is determined:

$$x^2 + y^2 \leq R^2. \quad \text{(Expression 12)}$$

Next, it is required under this approach that the laser energy distribution satisfy Equation 12 by simply stating that all the laser energy has to be on or inside the area defined by the circle. For scanning ablation, this means that each scan point (x,y) is checked by using Expression 12 during the surgery to verify its inclusion or exclusion as a point to be ablated. Using this known technique, all points outside of the circle of Equation 12 are excluded as an ablation point. during the surgery.

Expression 12 eliminates the need to solve for complicated Equations 7, 10, or 10' such that y is a function of x. Instead, the laser power distribution may be represented by $$n\Delta - Z_{g1}(x,y) + Z_{g2}(x,y) - c \leq 0 \quad \text{(Expression 13)}$$

or other, similar forms for different eye surface models. This means that the laser pulses will be directed only within and on the ellipse-like enclosing curve.

This newer procedure realizes the different diopter (curvature) changes in the x-axis and y-axis to correct for astigmatism and myopia or hyperopia together, without requiring the additional cylindrical ablation shown in FIG. 10.

Figure 11:
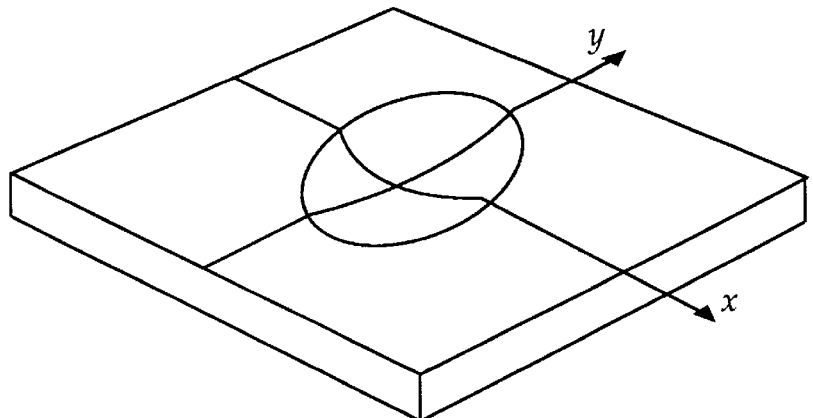
FIG. 11 is an illustration of a corneal surface of an eye having a conventional oval pattern ablation layer to correct for astigmatism in addition to simple myopia.

Reduction of the diameter in the x-axis direction at each and every layer depth to end up with an oval pattern is shown in FIG. 11. With the diameter squeezed in a certain mathematically determined fashion at different depths of ablation, the diopter change on the corneal surface will be more in the x-axis direction than in the y-axis direction. This process corrects astigmatic myopia.

In review, with the above procedure shown with respect to FIGS. 8A, 8B, and 11, the curvature change will be larger in the x-axis direction than in the y-axis direction. The total depth of ablation is the same as that of the counterpart ablation for simple myopia correction. The amount of tissue removal is less than that of the counterpart ablation for simple myopia correction, due to the reduced ablation dimension in the x-axis direction. The amount of tissue removal is also far less than that of the two-step procedure discussed above and shown in FIGS. 9 and 10.

The x-axis and y-axis have been arbitrarily chosen in this work. Thus, the procedure described here is applicable to symmetric astigmatic myopialhyperopla corrections at any angle.

Figure 15:
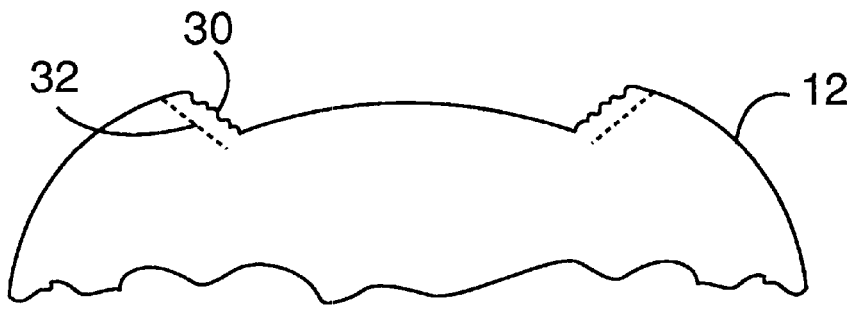
FIG. 15 is a side view of a cornea after conventional refractive surgery.

In accordance with the invention, it is preferable to use the torus model for the eye surface and consider the layered scan; i e., Expressions 9', 10' and 13. Expression 13 is used since it is much easier to solve than Equation 10'. It is noted that the effective ablation area for each layer might be smaller than the enclosed area by the solid curve. For example, since only laser pulse center points 34 (FIGS. 8A, 8B) that fall within or on the boundary of the curve 36 are used during the conventional surgery, corneal material near but outside the curve 36 may not be ablated. Depending on the distance d between each ablation point 34, on the same line scans the last point ablated may be just less that the distance d as shown in FIG. 8A(1). As shown in FIG. 8A(1), although the ablation layer boundary curve 36 defines the desired area for ablation, the actual ablation layer boundary 36 is somewhat smaller. Thus, the area actually ablated 36a is smaller than the entire area enclosed by the curve 36. The resulting corneal surface alteration may not be as precisely the same as predicted by the math model. Thus, with reference to FIG. 15, the cornea 12 may be ablated which results in wall surface 30, instead of a theoretical wall surface 32. An important aspect of the present invention is to provide a controllable apparatus and process to approach the theoretical ablation layer curve 36 more closely.

In accordance with the invention, Expression 13 is modified slightly so that the laser center points near but outside the curve 36 are included in the scan if they are close enough to the boundary, e.g., within d/2, where d is the distance between scan points 34.

To illustrate this point, consider the linear scan situation (rather than the circular scan). If the linear scan is taken along the direction of a p-axis (major axis), and a q-axis (minor axis) is orthogonal to the p-axis, then the transformations to x-y coordinates are given by:

$$x = x(p,q), \; y = y(p,q). \quad \text{(Equation 14)}$$

The exact expressions for x(p,q) and y(p,q) depend on the relative positions of the xy and pq coordinate systems. Expression 13 now becomes:

$$n\Delta + F(p,q) - c \leq 0 \quad \text{(Expression 15)}$$

where $$F(p,q) = -Z_{g1}(x(p,q), y(p,q)) + Z_{g2}(x(p,q), y(p,q)). \quad \text{(Expression 16)}$$

Expression 15 can be substituted by the following four expressions:

$$n\Delta + F(p+\delta, q+\delta) - c \leq 0, \quad \text{(Expression 15a)}$$

$$n\Delta + F(p+\delta, q-\delta) - c \leq 0, \quad \text{(Expression 15b)}$$

$$n\Delta + F(p-\delta, q+\delta) - c \leq 0, \quad \text{(Expression 15c)}$$

$$n\Delta + F(p-\delta, q-\delta) - c \leq 0. \quad \text{(Expression 15d)}$$

If it is required that each laser pulse position satisfy at least one of the four Expressions 15a–15d to be included in the scan, then not only points inside and on the curve defining the ablation layer, but also points that are outside the generally oval-shaped ablation layer by approximately a distance δ are nevertheless included in the predetermined surface layer to be ablated. Thus, according to the present invention, the laser beam is sometimes focused on points outside the defined ablation layer area. This provides an "integration" over the curve 36 to provide a total ablation which more closely approaches the theoretically desired resulting corneal shape.

It has been determined that a reasonably good choice for δ is half the scanning step size d. Therefore, points that are close enough to the boundary curve(i.e., within δ in the p or q directions) are included in the ablation, and points that are too far away from the curve (i.e., greater than δ in both the p and q directions) are omitted from the ablation. Therefore, the effective ablated area is closer to the area enclosed by the curve 36.

Figure 16:
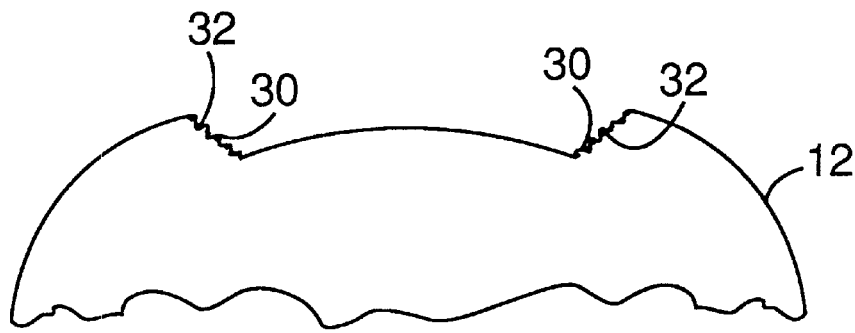
FIG. 16 is a side view of a cornea after refractive surgery according to the invention.

FIG. 16 depicts the corneal shape resulting, for ablation of the points outside but close to the ablation layer. As shown, since laser pulse center points outside the boundary of the curve are included in the ablation, wall 30 substantially coincides with theoretical wall 32 and results in a smoother, less jagged surface.

Figure 12:
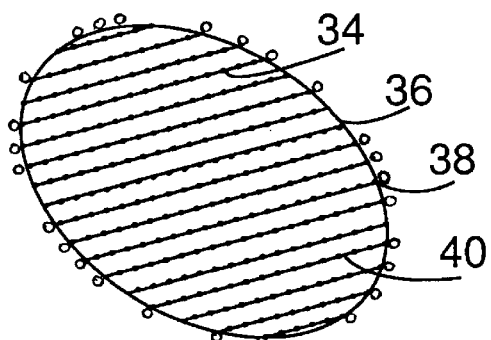
FIG. 12 is an illustration of a scanning pattern for a linear scan approach of the invention having random starting laser center points and which includes laser center points that are outside of but close to the boundary of the ablation layer.

The principles of the present invention can be expanded using other techniques. For example, a linear scan with random staring points is shown in FIG. 12. Only the points that satisfy any one of the Expressions 15a–15d are included in the ablation, as shown in FIG. 12. The points within the ablation layer curve 36 are depicted by dots 34, and the points outside but near enough to the ablation layer curve 36 are depicted by dots 38 enclosed by circles. Using a random start technique, the starting point for each scan line 40 is not regular, thus randomizing the scan. It is noted again that the laser pulse points 34 and 38 indicate the center of the laser beam and in actual practice the laser pulses have a predetermined spot size and overlap.

Figure 13:
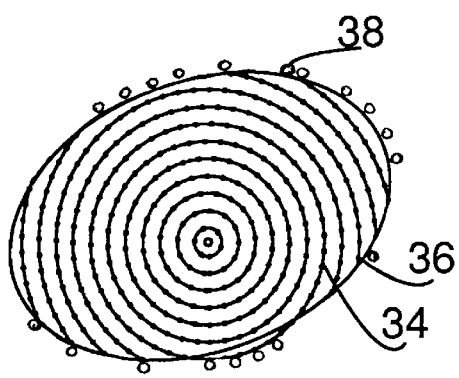
FIG. 13 is a illustration of a scanning pattern for a circular scan approach according to the invention having a random center location and including laser center points that are outside of but close to the ablation layer.

Another technique augmenting the application of the present invention is the use of a circular scan with a random center point, as shown in FIG. 13. The center of the circular scan can be any point other than the symmetrical center of the ablation layer, using this technique. The center of each layer to be ablated is placed randomly in the layer to minimize the accumulative effect when many layers are ablated. Again, points 34 within the ablation layer curve 36 are included in the scan together with encircled points 38 which are those points outside but near enough to the curve 36.

Figure 14:
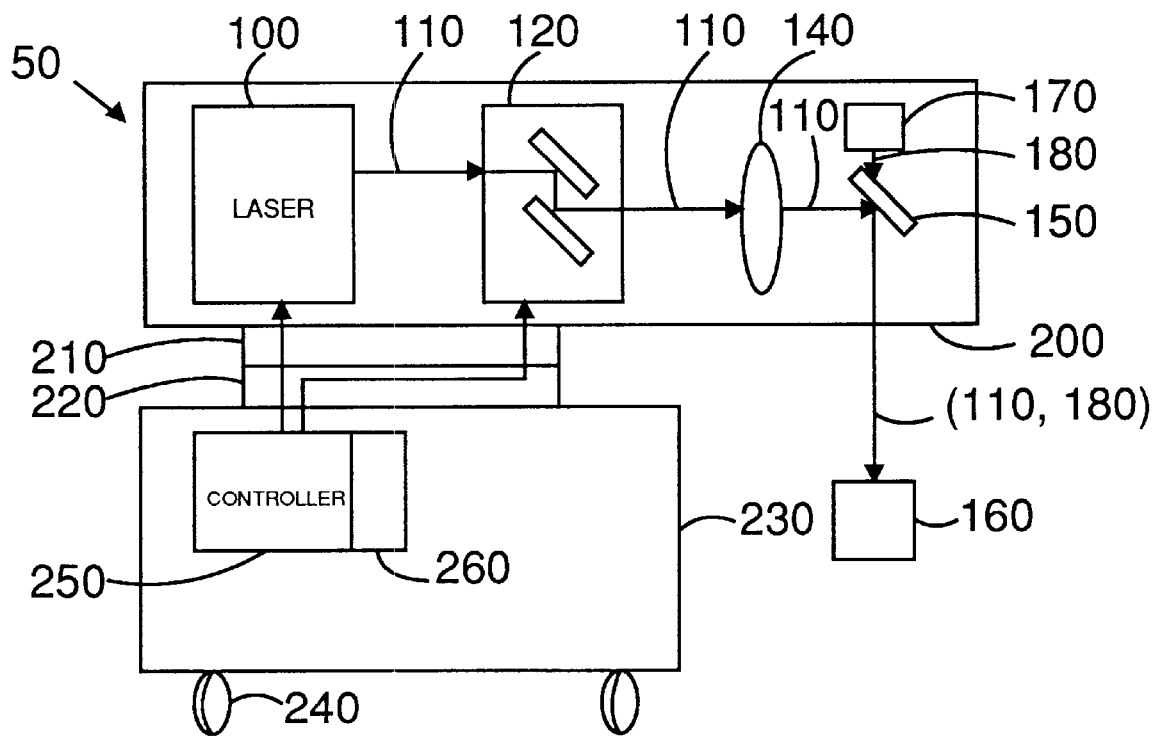
FIG. 14 is a schematic illustration of an apparatus for re-profiling a surface of the eye, provided in accordance with the invention.

Referring to FIG. 14, a refractive laser system 50 provided in accordance with the present invention is shown which is capable of performing the scan and ablation defined above. The system 50 comprises a laser 100 having UV (preferably 193–220 nm) or IR (0.7–3.2 µm) wavelength to generate a beam 110. A scanning device 120 capable of controllability changing the incident angle of the laser beam 110 passes the angled beam 110 to the focusing optics 140, onto a reflecting mirror 150, and onto target 160. The laser beam 110 preferably has an energy level less than 10 mJ/pulse. The target 160 is the cornea of an eye.

An aiming system 170 has a visible wavelength light beam (preferably from a laser diode or He—Ne laser)180 adjusted to be co-linear with the ablation laser beam 110 to define the normal incident angle. The basic laser head 200 is steered by a motorized stage for X and Y horizontal directions 210 and the vertical (height) direction 220 which assures the focusing beam spot size and concentration of the beam onto the cornea. The system 50 has a control panel 230 including a controller 250 for controlling the laser 100 and for controlling scanning mechanism 120 for controlling the angle of the beam 110, and for controlling all other aspects of system 50. Wheels 240 are provided to make the system 50 portable.

The basic laser head 200 and control panel 230 are of the type disclosed in U.S. Pat. No. 5,520,679, the content of which is hereby incorporated by reference into the present specification. However, in accordance with the invention, the controller 250 in the form of a microprocessor, digital signal processor, or microcontroller, includes in program memory 260 the expressions necessary to control the scanning mechanism 120 to ensure that the laser pulse center point positions may occur at locations inside, on, and outside of but substantially near the boundary of the mathematically defined ablation layer curve 36 (FIGS. 12, 13). Thus, the memory 260 includes the functions of Expressions 15a–15d defined above. The controller 250 also permits the scan to start in a random manner (linear scan) using a random center point (circular scan), or any other augmenting technique.

It can be appreciated by employing the apparatus of the invention having the inventive models, myopia, hyperopia, astigmatic myopia and astigmatic hyperopia conditions may be rectified in a manner that corresponds more closely to a mathematically defined curve selected to model the surface of the cornea to be ablated. This is possible since certain laser center points outside of the curve boundary are selected during ablation.

It has thus been seen that the objects of this invention have been fully and effectively accomplished. It will be realized, however, that the foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of ablating a surface area, comprising:

defining an ablation layer area having a boundary;

defining a plurality of ablation points to ablate a portion of said surface area substantially corresponding to an area defined by said ablation layer area;

providing a scanning mechanism to scan an ablating laser beam across said surface area, said scanning mechanism having a scanning step size;

determining whether a particular one of said plurality of ablation points is within said boundary of said ablation layer area, on said boundary of said ablation layer area, or outside said boundary of said ablation layer area;

scanning said ablating laser beam to move a center of said ablating laser beam to said particular one of said plurality of ablation points to ablate said particular one of said plurality of ablation points if said particular one of said plurality of ablation points is within said boundary of said ablation layer area, or on said boundary of said ablation layer area; and scanning said ablating laser beam to move a center of said ablating laser beam to said particular one of said plurality of ablation points to ablate said particular one of said plurality of ablation points if said particular one of said plurality of ablation points is outside said boundary of said ablation layer area, and if a distance between said particular one of said plurality of ablation points outside said boundary and said boundary is less than a predetermined distance less than said scanning step size.

2. The method of ablating according to claim 1, wherein:

said surface area is an area of corneal tissue.

3. The method of ablating according to claim 1, further comprising:

setting said predetermined distance to approximately half of said scanning step size.

4. The method of ablating according to claim 1, further comprising:

setting said predetermined distance to be equal to a δ; and ablating a particular one of said plurality of ablation points outside said boundary if said particular one of said plurality of ablation points outside said boundary satisfies at least one of following expressions:

$$n\Delta + F(p+\delta, q+\delta) - c \leq 0,$$

$$n\Delta + F(p+\delta, q-\delta) - c \leq 0,$$

$$n\Delta + F(p-\delta, q+\delta) - c \leq 0,$$

$$n\Delta + F(p-\delta, q-\delta) - c \leq 0,$$

where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, and where c is a constants.

5. The method of ablating according to claim 4, further comprising:
setting said δ to be equal to δ approximately half of said scanning step size.

6. The method of ablating according to claim 1, further comprising:
ablating a particular one of said plurality of ablation points outside said boundary if said particular one of said plurality of ablation points outside said boundary satisfies $n\Delta+F(p,q)-c \leq 0$, where $n\Delta$ is a change in thickness of an nth layer of the corneal surface to be ablated, where $F(p,q)=-Z_{g1}(x(p,q), y(p,q))+Z_{g2}(x(p,q), y(p,q))$, where $Z_{g1}$ and $Z_{g2}$ define final and initial corneal surfaces, respectively, where c is a constant, where said scanning mechanism performs a scan along a p-axis of said curve and a q-axis that is orthogonal to the p-axis, and where x and y represent x and y axis, respectively.

7. A method of ablating a surface area, comprising:
providing a scanning mechanism to scan an ablating laser beam across said surface area, said scanning mechanism having a scanning step size;
defining an ablation layer area having a boundary;
defining a plurality of first ablation points within said boundary of said ablation layer area, or on said boundary of said ablation layer area;
providing an integrating algorithm, said integrating algorithm defining a plurality of second ablation points that are outside said boundary of said ablation layer area, and are less than a predetermined distance less than said scanning step size apart from said boundary of said ablation layer area;
scanning said ablating laser beam to move a center of said ablating laser beam to each of said plurality of first ablation points and each of said plurality of second ablation points; and
ablating each of said plurality of first ablation points and each of said plurality of second ablation points.

8. The method of ablating according to claim 7, further comprising:
setting said predetermined distance to approximately half of said scanning step size.

9. The method of ablating a surface area according to claim 7, wherein:
said step of providing an integrating algorithm comprises:
providing an algorithm that determines whether to include an ablation point outside said boundary in said plurality of second ablation points by determining if said ablation point outside said boundary satisfies at least one of following expressions:

$n\Delta+F(p+,q+\delta)-c \leq 0$, $n\Delta+F(p+,q-\delta)-c \leq 0$, $n\Delta+F(p-,q+\delta)-c \leq 0$, $n\Delta+F(p-,q-\delta)-c \leq 0$, where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, and where c and δ are constants.

10. The method of ablating according to claim 9, further comprising:
setting said δ to be equal to δ approximately half of said scanning step size.

11. The method of ablating according to claim 7, further comprising:
ablating a particular one of said plurality of ablation points outside said boundary if said particular one of said plurality of ablation points outside said boundary satisfies $n\Delta+F(p,q)-c \leq 0$, where $n\Delta$ is a change in thickness of an nth layer of the corneal surface to be ablated, where $F(p,q)=-Z_{g1}(x(p,q), y(p,q))+Z_{g2}(x(p,q), y(p,q))$, where $Z_{g1}$ and $Z_{g2}$ define final and initial corneal surfaces, respectively, where c is a constant, where said scanning mechanism perforrms a scan along a p-axis of said curve and a q-axis that is orthogonal to the p-axis, and where x and y represent x and y axis, respectively.

12. A method of ablating a portion of a surface area using an ablating laser beam scanned across said surface area using a scanning mechanism having a scanning step size, said portion of a surface area being substantially defined by an ablation layer area having a boundary, said portion of said surface area including a plurality of ablation points, said method comprising:
determining whether a particular one of said plurality of ablation points is within said boundary of said ablation layer area, on said boundary of said ablation layer area, or outside said boundary of said ablation layer area;
scanning said ablating laser beam to move a center of said ablating laser beam to said particular one of said plurality of ablation points to ablate said particular one of said plurality of ablation points if said particular one of said plurality of ablation points is within said boundary of said ablation layer area, or on said boundary of said ablation layer area; and
scanning said ablating laser beam to move a center of said ablating laser beam to said particular one of said plurality of ablation points to ablate said particular one of said plurality of ablation points if said particular one of said plurality of ablation points is outside said boundary of said ablation layer area, and if a distance between said particular one of said plurality of ablation points outside said boundary and said boundary is less than a predetermined distance less than said scanning step size.

13. The method of ablating according to claim 12, further comprising:
setting said predetermined distance to approximately half of said scanning step size.

14. The method of ablating according to claim 12, further comprising:
setting said predetermined distance to be equal to a δ; and
ablating a particular one of said plurality of ablation points outside said boundary if said particular one of said plurality of ablation points outside said boundary satisfies at least one of following expressions:

$n\Delta+F(p+\delta,q+\delta)-c \leq 0$, $n\Delta+F(p+\delta,q-\delta)-c \leq 0$, $n\Delta+F(p-\delta,q+\delta)-c \leq 0$, $n\Delta+F(p-\delta,q-\delta)-c \leq 0$, where $n\Delta$ is a change in thickness of an nth layer of the corneal surface to be ablated, where $F(p,q)=-Z_{g1}(x$ (p,q), y(p,q))+$Z_{g2}$ (x(p,q),y(p,q)), where $Z_{g1}$ and $Z_{g2}$ define final and initial corneal surfaces, respectively, and where c is a constants.

15. The method of ablating according to claim 14, further comprising:

setting said a to be equal to approximately half of said scanning step size.

16. The method of ablating according to claim 12, further comprising:

ablating a particular one of said plurality of ablation points outside said boundary if said particular one of said plurality of ablation points outside said boundary satisfies $n\Delta+F(p,q)-c\leq 0$, where $n\Delta$ is a change in thickness of an nth layer of the corneal surface to be ablated, where $F(p,q)=-Z_{g1}(x(p,q), y(p,q))+Z_{g2}$ (x(p,q),y(p,q)), where $Z_{g1}$ and $Z_{g2}$ define final and initial corneal surfaces, respectively, where c is a constant, where said scanning mechanism performs a scan along a p-axis of said curve and a q-axis that is orthogonal to the p-axis, and where x and y represent x and y axis, respectively.

17. The method of ablating according to claim 12, wherein:

said surface area is an area of corneal tissue.

18. A method of determining a plurality of ablation points for ablating a portion of a layer of a surface area to substantially achieve a desired post ablation profile of said portion of said layer of said surface area, comprising:

determining an ideal ablation layer area having a boundary, said ideal ablation layer area defining an area corresponding to said desired post ablation profile of said surface area portion of said layer of said surface area;

determining a plurality of first ablation points within said boundary, said plurality of first ablation points having a plurality of first outermost ablation points with respect to a symmetrical center of said ideal ablation layer, said plurality of first outermost ablation points defining a first actual ablation layer area that is smaller than said ideal ablation layer area;

determining a plurality of second ablation points, each of said plurality of second ablation points being disposed outside of said boundary;

determining an integrated sum of said first plurality of ablation points and said second plurality of ablation points, said integrated sum having a plurality of second outermost ablation points with respect to said symmetrical center of said ideal ablation layer, said plurality of second outermost ablation points defining a second actual ablation layer area that more closely matches said ideal ablation layer area than said first actual ablation layer area.

19. The method of determining a plurality of ablation points according to claim 18, wherein:

said step of determining said plurality of second ablation points comprises:

including an ablation point outside said boundary in said plurality of second ablation points if said ablation point outside said boundary satisfies at least one of following expressions:

$n\Delta+F(p+\delta,q+\delta)-c\leq 0$, $n\Delta+F(p+\delta,q-\delta)-c\leq 0$, $n\Delta+F(p-\delta,q+\delta)-c\leq 0$, $n\Delta+F(p-\delta,q-\delta)-c\leq 0$, where $n\Delta$ is a change in thickness of an nth layer of the corneal surface to be ablated, where $F(p,q)=-Z_{g1}(x(p,q), y(p,q))+Z_{g2}$ (x(p,q),y(p,q)), where $Z_{g1}$ and $Z_{g2}$ define final and initial corneal surfaces, respectively, and where c and g are constants.

20. The method of determining a plurality of ablation points according to claim 19, further comprising:

setting said δ to be equal to approximately half of said scanning step size.

21. The method of determining a plurality of ablation points according to claim 18, wherein:

said step of determining said plurality of second ablation points comprises:

including an ablation point outside said boundary in said plurality of second ablation points if said ablation point outside said boundary satisfies $n\Delta+F(p,q)-c\leq 0$, where $n\Delta$ is a change in thickness of an nth layer of the corneal surface to be ablated, where $F(p,q)=-Z_{g1}(x(p,q), y(p,q))+Z_{g2}$ (x(p,q),y(p,q)), where $Z_{g1}$ and $Z_{g2}$ define final and initial corneal surfaces, respectively, where c is a constant, where said scanning mechanism performs a scan along a p-axis of said curve and a q-axis that is orthogonal to the p-axis, and where x and y represent x and y axis, respectively.

22. The method of determining a plurality of ablation points according to claim 18, wherein:

said step of determining said plurality of second ablation points comprises:

providing an integration algorithm, said integration algorithm adapted to include an ablation point outside said boundary in said plurality of second ablation points if said ablation point outside said boundary are within a predetermined distance from said boundary.

23. The method of determining a plurality of ablation points according to claim 22, further comprising:

providing a scanning mechanism to scan an ablating laser beam across said surface area, said scanning mechanism having a scanning step size.

24. The method of determining a plurality of ablation points according to claim 23, wherein:

said predetermined distance is approximately half of said scanning step size.

25. The method of determining a plurality of ablation points according to claim 18, wherein:

said surface area is an area of corneal tissue.

26. The method of determining a plurality of ablation points according to claim 23, wherein:

said step of providing said scanning mechanism comprises:

providing a scanning mechanism that scans a circular pattern of concentric output beam spots, wherein a center of said circular pattern is placed randomly on said portion of said layer of said surface area.

27. The method of determining a plurality of ablation points according to claim 23, wherein:

said step of providing said scanning mechanism comprises:

providing said scanning mechanism that scans a linear pattern of output beam spots, wherein a starting point of each line of said liner pattern is randomly selected.

28. An apparatus for scanning an ablating laser beam across a surface area to ablate said surface area to substantially achieve a desired post ablation profile of said surface area, said desired post ablation profile of said surface area being defined by an ideal ablation area having a boundary, said ideal ablation area being approximated by a first actual ablation area that is smaller than said ideal ablation area, said first actual ablation area being defined by a plurality of first outermost ablation points, said plurality of first outermost ablation points being outermost ones of a plurality of first ablation points with respect to a symmetrical center of said ideal ablation area, each of said plurality of first ablation points being disposed within or on said boundary, said apparatus comprising:

a controller adapted to produce a scanner control signal in accordance with a scanning pattern;

a scanning mechanism adapted to move said laser beam across an ablation layer are of said surface area in response to said scanner control signal received from said controller; and an integrating algorithm adapted to produce said scanning pattern that comprises an integrated sum of said first plurality of ablation points and a plurality of second ablation points, each of said plurality of second ablation points being disposed outside of said boundary, a plurality of second outermost ablation points defining a second actual ablation area, said plurality of second outermost ablation points being outermost ones of said plurality of second ablation with respect to said symmetrical center of said ideal ablation area, said second actual ablation area matching said ideal ablation area more closely than said first actual ablation area.

29. The apparatus for scanning an ablating laser beam across a surface area according to claim 28, wherein:

said integrating algorithm is adapted to include an ablation point outside said boundary in said plurality of second ablation points if said ablation point outside said boundary satisfies at least one of following expressions:

$$n\Delta+F(p+\delta,q+\delta)-c \leq 0,$$

$$n\Delta+F(p+\delta,q-\delta)-c \leq 0,$$

$$n\Delta+F(p-\delta,q+\delta)-c \leq 0,$$

$$n\Delta+F(p-\delta,q-\delta)-c \leq 0,$$

where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, and where c and rare constants.

30. The apparatus for scanning an ablating laser beam across a surface area according to claim 29, wherein:

said scanning mechanism has a scanning step size.

31. The apparatus for scanning an ablating laser beam across a surface area according to claim 30, wherein:

said $\delta$ to be equal to approximately half of said scanning step size.

32. The apparatus for scanning an ablating laser beam across a surface area according to claim 28, wherein:

said integrating algorithm is adapted to include an ablation point outside said boundary in said plurality of second ablation points if said said ablation point outside said boundary are within a predetermined distance from said boundary.

33. The apparatus for scanning an ablating laser beam across a surface area according to claim 32, wherein:

said scanning mechanism has a scanning step size.

34. The apparatus for scanning an ablating laser beam across a surface area according to claim 33, wherein:

said predetermined distance is approximately half of said scanning step size.

35. The apparatus for scanning an ablating laser beam across a surface area according to claim 28, wherein:

said surface area is an area of corneal tissue.

36. The apparatus for scanning an ablating laser beam across a surface area according to claim 28, wherein:

said integrating algorithm is adapted to include an ablation point outside said boundary in said plurality of second ablation points if said ablation point outside said boundary satisfies $n\Delta+F(p,q)-c \leq 0$, where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, where c is a constant, where said scanning mechanism performs a scan along a p-axis of said curve and a q-axis that is orthogonal to the p-axis, and where x and y represent x and y axis, respectively.

37. The apparatus for scanning an ablating laser beam across a surface area according to claim 28, further comprising:

a pulsed laser.

38. The apparatus for scanning an ablating laser beam across a surface area according to claim 37, wherein:

said pulsed laser is a UV pulsed laser having an energy level less than 10 mJ/pulse.

39. The apparatus for scanning an ablating laser beam across a surface area according to claim 37, wherein:

said pulsed laser has an output wavelength between 193 and 220 nanometers.

40. The apparatus for scanning an ablating laser beam across a surface area according to claim 28, wherein:

said scanning mechanism is adapted and arranged to scan a circular pattern of concentric circles with a center of said circles being non-co-axial with said symmetrical center of said ideal ablation area.

41. The apparatus for scanning an ablating laser beam across a surface area according to claim 28, wherein:

said scanning mechanism is constructed and arranged to scan a linear pattern of parallel lines of ablation points, wherein a starting point of each parallel line of ablation points is randomly selected with respect to a distance from said boundary of said ideal ablation area.

42. An apparatus for scanning an ablating laser beam across a portion of a surface area defined by an ablation area having a boundary, comprising:

a controller to produce a scan control signal in accordance with an integrated sum of a plurality of ablation points;

a scanning mechanism adapted to move said laser beam across an ablation layer area of said surface area in response to said scan control signal received from said controller, said scanning mechanism having a scanning step size; and a memory having an integrating algorithm to produce said integrated sum of said plurality of ablation points that includes ones of said plurality of ablation points within or on said boundary, said integrated sum of said plurality of ablation points further including ones of said plurality of ablation points outside said boundary if said ones of plurality of ablation points outside said boundary are within a predetermined distance that is less than said scanning step size from said boundary.

43. The apparatus for scanning an ablating laser beam according to claim 42, wherein:

said predetermined distance is approximately half of said scanning step size.

44. The apparatus for scanning an ablating laser beam according to claim 42, wherein:

said surface area is an area of corneal tissue.

45. The apparatus for scanning an ablating laser beam according to claim 42, wherein:

said integrating algorithm comprises:

an algorithm to include an ablation point outside said boundary in said plurality of second ablation points if said ablation point outside said boundary satisfies at least one of following expressions:

$n\Delta+F(p+\delta,q+\delta)-c \leq 0,$ $n\Delta+F(p+\delta,q-\delta)-c \leq 0,$ $n\Delta+F(p-\delta,q+\delta)-c \leq 0,$ $n\Delta+F(p-\delta,q-\delta)-c \leq 0,$ where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, and where c and $\delta$ are constants.

46. The apparatus for scanning an ablating laser beam according to claim 45, wherein:

said $\delta$ to be equal to approximately half of said scanning step size.

47. The apparatus for scanning an ablating laser beam according to claim 42, wherein:

said integrating algorithm is adapted to include an ablation point outside said boundary in said plurality of second ablation points if said ablation point outside said boundary satisfies $n\Delta+F(p,q)-c \leq 0$, where $n\Delta$ is a change in thickness of an nth layer of the corneal surface to be ablated, where $F(p,q)=-Z_{g1}(x(p,q), y(p,q))+Z_{g2}(x(p,q),y(p,q))$, where $Z_{g1}$ and $Z_{g2}$ define final and initial corneal surfaces, respectively, where c is a constant, where said scanning mechanism performs a scan along a p-axis of said curve and a q-axis that is orthogonal to the p-axis, and where x and y represent x and y axis, respectively.

48. The apparatus for scanning an ablating laser beam according to claim 42, further comprising:

a pulsed laser.

49. The apparatus for scanning an ablating laser beam according to claim 48, wherein:

said pulsed laser is a UV pulsed laser having an energy level less than 10 mJ/pulse.

50. The apparatus for scanning an ablating laser beam according to claim 48, wherein:

said pulsed laser has an output wavelength between 193 and 220 nanometers.

51. The apparatus for scanning an ablating laser beam across a surface area according to claim 42, wherein:

said scanning mechanism is adapted and arranged to scan a circular pattern of concentric circles with a center of said circles being non-co-axial with a symmetrical center of said ablation area.

52. The apparatus for scanning an ablating laser beam across a surface area according to claim 42, wherein:

said scanning mechanism is adapted and arranged to scan a linear pattern of parallel lines of ablation points, wherein a starting point of each parallel line of ablation points is randomly selected with respect to a distance from said boundary of said ablation area.

* * * * *